United States Patent [19]

McCulloch et al.

[11] Patent Number: 5,107,052

[45] Date of Patent: Apr. 21, 1992

[54] EXTRACTION OF DIMETHYL PARAFFINS FROM ISOMERATES

[75] Inventors: Beth McCulloch, Barrington; James R. Lansbarkis, Bensenville; Srikantiah Raghuram, Darien; Robert S. Haizmann, Rolling Meadows, all of Ill.

[73] Assignee: UOP, Des Plaines, Ill.

[21] Appl. No.: 636,646

[22] Filed: Dec. 31, 1990

[51] Int. Cl.⁵ .......................... C07C 5/13; C07C 7/12
[52] U.S. Cl. ................... 585/738; 585/820; 585/826; 585/825
[58] Field of Search ................ 585/738, 820, 826, 825

[56] References Cited

U.S. PATENT DOCUMENTS

| | | | |
|---|---|---|---|
| 2,935,539 | 5/1960 | Gladrow et al. | 585/820 |
| 2,966,528 | 12/1960 | Haensel | 260/666 |
| 2,985,589 | 5/1961 | Broughton et al. | 210/34 |
| 3,040,777 | 6/1962 | Carson et al. | 137/625.15 |
| 3,422,848 | 1/1969 | Liebman et al. | 137/625.15 |
| 3,442,794 | 5/1969 | Van Helden et al. | 208/111 |
| 3,706,813 | 12/1972 | Neuzil | 260/676 MS |
| 3,755,144 | 8/1973 | Asselin | 208/95 |
| 3,888,939 | 6/1975 | Rosback | 260/677 |
| 4,310,440 | 1/1982 | Wilson et al. | 252/435 |
| 4,440,871 | 4/1984 | Lok et al. | 502/214 |
| 4,567,029 | 1/1986 | Wilson et al. | 423/306 |
| 4,717,784 | 1/1988 | Stem et al. | 585/738 |
| 4,758,419 | 7/1988 | Lok et al. | 423/306 |
| 4,804,803 | 2/1989 | Schmidt et al. | 585/748 |
| 4,834,958 | 5/1989 | Zones | 423/277 |
| 4,855,529 | 8/1989 | Stem et al. | 585/737 |

OTHER PUBLICATIONS

Van Nordstrand et al., *Perspectives in Molecular Sieve Science*, Flank and Whyte, Ed., Chap. 15 (1988), pp. 236–245.

"Continuous Adsorptive Processing—A New Separation Technique", D. B. Broughton presented at the 34th Annual Meeting of the Society of Chemical Engineers at Tokyo on Apr. 2, 1969.

*Primary Examiner*—Anthony McFarlane
*Assistant Examiner*—Nhat Phan
*Attorney, Agent, or Firm*—Thomas K. McBride; John F. Spears, Jr.; Jack H. Hall

[57] ABSTRACT

The invention relates to the production of high octane fuels including a process for separating the high octane components for the gasoline pool from lower octane components, which are recycled to an isomerization reaction by adsorptively separating dimethyl paraffins from an isomerate with an aluminophosphate zeolite and SSZ-24, an all-silica zeolite adsorbent isostructural with $AlPO_4$-5, and a $C_{6-10}$ normal paraffin desorbent. The lower octane components of the isomerate, normal paraffins and mono-branched paraffins, are recycled to the isomerization reaction zone for further conversion to multi-branched paraffins. The useful aluminophosphates are SAPO-5, $AlPO_4$-5 MgAPO-5 and MAPSO-5.

5 Claims, 1 Drawing Sheet

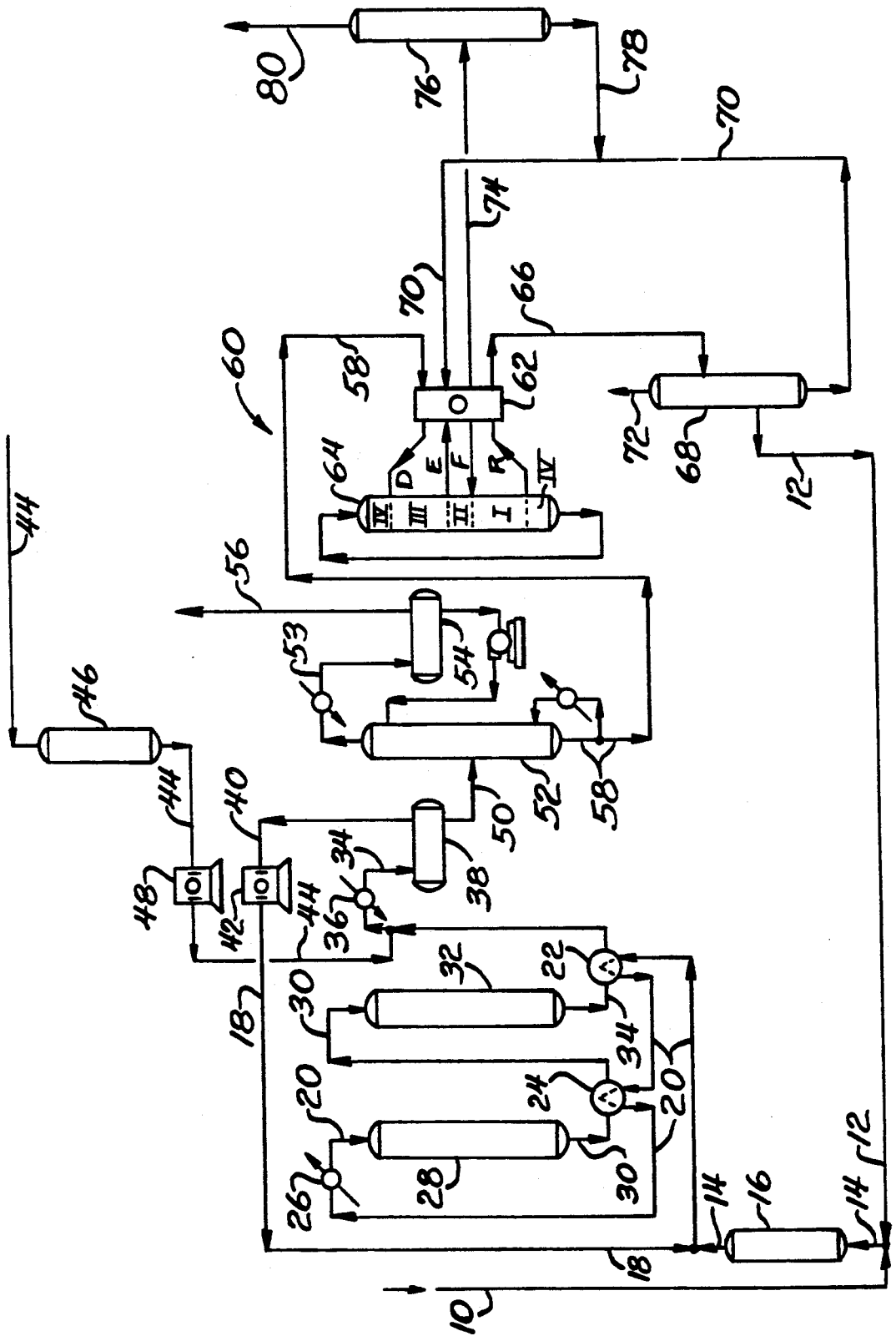

EXTRACTION OF DIMETHYL PARAFFINS FROM ISOMERATES

FIELD OF THE INVENTION

The invention relates to the production of high octane fuels including associated fields of isomerization of naphtha streams and adsorptive separation of an isomerate into its higher octane components, to be used for enhancing the gasoline pool, and its lower octane components, which can be recycled to the isomerization reaction step to increase the yield of the higher octane components.

BACKGROUND OF THE INVENTION

Light straight run naphtha, virgin naphtha and other refinery streams containing $C_5$ and $C_6$ paraffins, are useful sources of blending stock for gasoline pools, but, under current market conditions and ecological considerations, it is necessary to raise the Research Octane Number (RON) of the stock to about 85 to 94 (RON), without the addition of alkyl lead compounds. Since the phase-out of lead compounds began, refiners have relied on isomerization and reforming, e.g., platforming, steps to increase the octane to above about 80 RON and further, have integrated separation processes to separate the isomerate or reformate into higher and lower octane fractions, with the higher octane fraction typically about 90 RON, being sent to the gasoline pool. The lower octane fraction(s) may be recycled to the isomerization step for further conversion and higher yields of multi-branched, high octane paraffins.

In one approach to the upgrading of isomerate streams, U.S. Pat. Nos. 4,717,784 and 4,855,529 disclose similar processes for isomerizing a hydrocarbon feed and separating the dimethyl branched paraffins produced in the reaction from the n-paraffins and mono-methyl branched paraffins produced by utilizing a size- or shape-selective adsorbent. In the adsorptive separation step, the straight chain and singly branched paraffins are adsorbed into the pores of the molecular sieve while the more highly branched paraffins are excluded from entering the pores. The selectively adsorbed straight chain paraffins and/or the singly branched paraffins are recycled to the isomerization zone for further conversion to more highly branched paraffins. In this separation, the useful adsorbents have pore sizes in the range from $4.5 \times 4.5$ Å to $5.5 \times 5.5$ Å which exclude the di-branched paraffins from the pores of the molecular sieve. The preferred desorbent in the processes is hydrogen. The patentees teach that only sieves within this range are operative and others having pore sizes outside the range are too small or too large to perform the separation.

Neuzil U.S. Pat. No. 3,706,813 discloses the separation of dimethyl butanes from methyl pentanes and normal hexanes by selectively adsorbing the multi-branched components on barium-exchanged X or Y zeolites containing from 5–8% (wt.) water. However, adsorbents requiring these high levels of water could not be used for the instant process, because the isomerization catalysts are quickly deactivated by the presence of moisture. In the process of Neuzil, the multi-branched paraffin extract product would be contaminated with water removed from the adsorbent and, hence, could not be recycled to the isomerization reaction zone without first drying the extract stream. The process of our invention avoids this problem since the adsorbents of the invention are capable of selectively adsorbing the dialkyl paraffins without requiring the presence of water. Furthermore, the preferred isoparaffin desorbents were not effective as desorbents in applicants' process, since no separation could be observed when iso-paraffins were used.

Van Nordstrand et al, *Perspectives in Molecular Sieve Science*, Flank and Whyte, Ed., Chap. 15 (1988) pp 236–245 found that SAPO-5, $AlPO_4$-5 and SSZ-24 have a preference for adsorbing 2,2-dimethyl butane over n-hexane. The data obtained by the "Pore Probe" technique of Santilli (Reference No. 20 of Van Nordstrand et al), indicate intermediate selectivity for 3-methyl pentane. Nothing is contained in the disclosure regarding desorbents necessary for a continuous adsorptive separation process.

Isomerization processes for converting normal paraffins to mono-and di- or more highly branched chain paraffins are commonly used as a method for increasing the octane rating of refinery streams containing normal paraffins. Illustrative of the isomerization process are U.S. Pat. Nos. 3,755,144 to Asselin and 2,966,528 to Haensel.

U.S. Pat. No. 3,755,144 also discloses the separation of normal paraffins from the isomerization reactor effluent using a molecular sieve in a simulated moving bed system and recycling the normal paraffins to the isomerization reactor after recovering the desorbent. Iso-hexane is recovered from the extract in a deisohexanizer column and recycled to the isomerization reactor; isopentane and dimethyl butane are taken overhead while cyclic paraffins are recovered in the bottoms of the deisohexanizer. U.S. Pat. No. 2,966,528 further discloses a swing bed system operating under liquid phase conditions for the separation of normal hydrocarbons from branched hydrocarbons in which the normal hydrocarbons are selectively absorbed and desorbed from the adsorbent with a normal paraffin desorbent.

Accordingly, it is an object of the invention to provide a process for continuously separating di-branched paraffins from normal paraffins and mono-branched paraffins produced by an isomerization reaction with a particular adsorbent/desorbent combination by which the di-branched paraffins having a higher octane number are selectively adsorbed onto the adsorbent and low octane components, mono-branched paraffins and normal paraffins, are relatively selectively non-adsorbed by the adsorbent and are recovered from the non-selective void volume as raffinate. The low octane raffinate components are recycled to the isomerization step for further upgrading. The high octane di-branched paraffins are desorbed from the selective pore volume by a carefully selected desorbent. It is a further object of this invention to provide a novel process for combining and integrating an isomerization reaction with a continuous adsorptive separation process for enhanced octane rating of the product stream.

SUMMARY OF THE INVENTION

This invention provides a method for separating an isomerization feed stream into a fraction having components high in octane value and a fraction low in octane value. The high octane product containing the highly branched paraffins, e.g., dimethyl paraffins, and cyclic paraffins, in this isomerate feed stream, is valuable since the addition thereof to the gasoline pool will increase the overall octane value of the pool. The low octane fraction, containing monomethyl paraffins and normal paraffins, can be recycled to the isomerization process and combined with fresh feed for conversion to additional highly branched paraffins.

More specifically, the invention encompasses a process for producing a high octane hydrocarbon stream comprising: (a) introducing a paraffin hydrocarbon feed stream comprising $C_{4-6}$ paraffins into an isomerization zone maintained at isomerization conditions and containing an isomerization catalyst; (b) contacting the feed stream with the catalyst to produce an isomerate comprising dimethyl paraffins, monomethyl paraffins and normal paraffins; (c) passing the isomerate to a separation zone and contacting the isomerate with an adsorbent having pores large enough to admit all components of the isomerate and having selectivity for preferentially adsorbing the dimethyl paraffins and not adsorbing the monomethyl paraffins and normal paraffins; (d) removing a first stream comprising the non-adsorbed monomethyl paraffins and normal paraffins; (e) introducing a desorbent to the separation zone to desorb the adsorbed dimethyl paraffins from the adsorbent; (f) recovering a second stream comprising the desorbed dimethyl paraffins; and (g) recycling the first stream to the isomerization zone. Preferably, the water content of the adsorbent is below 2% measured by loss on ignition (LOI) at 900° C.

The method of separation comprises contacting the isomerate stream with an adsorbent selected from the group of SAPO-5, AlPO$_4$-5, SSZ-24, MgAPO-5 and MAPSO-5, selectively adsorbing the more highly branched paraffins and cyclic paraffins onto the adsorbent, removing the monoalkyl paraffins and normal paraffins from the adsorbent, desorbing the adsorbed cyclic paraffins and dialkyl paraffins by desorption with a desorbent comprising normal paraffins having 6 to 10 carbon atoms. The preferred desorbent is n-heptane.

In a further embodiment, the raffinate stream is separated by fractionation to remove octane-enhancing iso-pentane from the low octane fraction from the separation process at the same time the desorbent is removed from the raffinate stream for recycle to the separation zone. An increase of about 5 Research Octane Numbers in the dimethyl paraffin product can be obtained with only slightly lowered yield using this process compared with prior processes combining isomerization and adsorptive separation using zeolitic molecular sieves.

BRIEF DESCRIPTION OF THE DRAWING

FIG. 1 is a schematic diagram with a flow scheme for a combined isomerization and liquid phase adsorption separation process in accordance with this invention.

DETAILED DESCRIPTION OF THE INVENTION

An understanding of the combined process for the isomerization of $C_5$ and $C_6$ hydrocarbons and separation of the higher octane di-branched paraffin components from lower octane mono-branched and normal paraffin compounds with an aluminophosphate adsorbent and $C_{6-10}$ n-paraffin desorbent and recycle of mono-branched and di-branched paraffins to the isomerization zone can be obtained from FIG. 1. In FIG. 1, the $C_5$ and $C_6$ charge stock enters the process through a line 10 where it is combined with a recycle stream 12 that supplies recycled $C_5$ and $C_6$ monomethyl paraffins and normal paraffins to the isomerization zone. Line 14 carries the combined feed of charge and recycle to a dryer 16 after which it is combined with a recycle gas stream containing hydrogen carried by line 18. A line 20 carries the hydrogen and combined feed through a series of heat exchangers 22 and 24 that heat the feed prior to its passing through a heater 26 which raises the temperature of the mixture to the final initial reaction temperature. The fully heated hydrogen and charge mixture enter a reactor 28 that contains isomerization catalyst to perform an initial conversion of normal paraffins to iso-paraffins along with any exothermic reaction, such as the hydrogenation of olefins. Effluent from reactor 28 is carried by line 30 through exchanger 24 which cools the partially converted mixture before entering a second reactor 32 where the partially converted mixture is again contacted with isomerization catalyst at lower temperatures that favor the equilibrium conversion of normal paraffins to iso-paraffins and di-branched paraffins, e.g., dimethyl butanes and dimethyl pentanes. Effluent from reactor 32 is carried by line 34 through exchanger 22 and a condenser 36 that cools the isomerization effluent for the recovery of hydrogen and other light gases in a separator 38. A recycle gas stream rich in hydrogen is taken by line 40 from separator 38, recompressed in a compressor 42, and transferred by line 18 for combination with the feed. Any additional hydrogen needed for the process is supplied by a make-up hydrogen source brought into the process by line 44. A dryer 46, and a compressor 48 along the path of line 44, dry and bring the hydrogen up to process pressure before it is introduced into line 34. The hydrogen-depleted effluent from the isomerization zone is taken from separator 38 by line 50 to a stabilizer column 52. The stabilizer column removes all light gases and has a cut point that is adjusted for the removal of substantially all of the normal butane, although in some instances, it may be advantageous to adjust conditions for removal of iso-pentane, as will be referred to hereinafter. In the latter case, the iso-pentane can then be separated from hydrogen gas, which is recycled to the reactor, and from other light components and added to the gasoline pool. The overhead is transferred by a line 53 to a drum 54 from which a light gas stream is taken by line 56 and withdrawn from the process. The bottoms from the stabilizer 52 contain a mixture of normal paraffins, methyl paraffins and dimethyl paraffins. A line 58 transfers the stabilizer bottoms to an adsorption separation zone 60, which is preferably a simulated moving bed such as disclosed in Broughton U.S. Pat. No. 2,985,589.

In the simulated moving bed, the paraffins and monoalkyl paraffins in the effluent from the isomerization zone, having low octane numbers, are separated from higher octane components and are recycled to the isomerization zone for further reaction and upgrading to more highly branched paraffins. The higher octane product, di-branched paraffins, is recovered from the extract by fractionation and directed to the gasoline pool while the desorbent is recycled to the separation zone. Line 58 carrying the feed mixture to the adsorption section 60 is directly connected to a rotary valve 62 which simulates the movement of adsorbent in an adsorbent chamber 64 by the changing of inlet and outlet points in a manner hereinafter described. The adsorption separation zone 60 operates by contacting the feed mixture from line 58 with adsorbent material in adsorbent chamber 64 to provide a raffinate stream which is carried from rotary valve 62 by line 66. The raffinate stream contains normal paraffins, iso-paraffins and desorbent material which enter a combined raffinate/deisopentanizer column 68 that separates the material in the raffinate stream into a desorbent stream taken from the bottom of raffinate column 68 via line 70, an overhead product stream 72 of iso-pentane, which is added to the gasoline pool, and an intermediate cut comprising normal $C_5$ and $C_6$ paraffins and $C_6$ monomethyl paraffins to provide the previously described recycle stream 12. Line 70 transfers desorbent material to rotary valve 62 for its reuse in continuously displacing extract components from adsorbent chamber 64. If iso-pentane is removed with the light component in the reactor effluent in stabilizer 54, as previously stated, a conventional raffinate fractionator may be used instead of raffinate/deisopentanizer column 68.

Extract components recovered from adsorbent chamber 64 are directed by the rotary valve through line 74 to the extract column 76 where desorbent is taken in the bottoms stream via line 78 and returned to the adsorption separation zone 60 via line 70. The overhead stream 80 contains dimethyl paraffin products having an octane rating of at least about 88 to 90 RON. The octane rating of the overhead stream 80 will typically be about 5 numbers (RON) higher than prior combined processes using zeolitic 5A adsorbent in the adsorption separation zone.

The feed to the isomerization process may be a refinery stream, such as a light straight run naphtha or virgin naphtha, rich in $C_4$, $C_5$ and $C_6$ normal paraffins. The feed mixture may also contain a major or minor portion of branched chain hydrocarbons, especially iso-paraffins having a number of carbon atoms corresponding to the normal paraffins. Preferred feedstocks are substantially pure normal paraffin streams having from 4–6 carbon atoms or a mixture of such substantially pure normal paraffins. Other useful feedstocks include light natural gasoline, gas oil condensates, light raffinates, light reformate, light hydrocarbons, and straight-run distillates having distillation end points of about 77° C. (170° F.) and containing substantial quantities of $C_4$–$C_6$ paraffins. The feed may also contain low concentrations of unsaturated hydrocarbons and heavier hydrocarbons. The concentration of these materials should be limited to 10 wt. % for unsaturated compounds and 20 wt. % for heavier hydrocarbons in order to restrict hydrogen consumption in cracking reactions. The feed and any paraffin recycle are combined and typically enter the isomerization zone with a hydrogen recycle stream. Ranges and typical feed compositions suitable for practicing the invention include:

TABLE 1

| Component | Range Liq. Vol. % (Mole %) | Typical Composition (LSRN) (Vol. %) |
|---|---|---|
| n—$C_4$ | 0 to 3 | (1.04) |
| i—$C_5$ | 10 to 30 | (14.7) |
| n—$C_5$ | 10 to 40 | (28.3) |
| Cyclopentane | 0 to 5 | (1.7) |
| 2,2-dimethyl butane (DMB) | 0 to 10 | (0.4) |
| 2,3-DMB | 0 to 15 | (1.6) |
| 2-Methyl Pentane (MP) | 0 to 30 | (10.4) |
| 3 MP | 0 to 30 | (8.2) |
| n-hexane ($C_6$) | 10 to 30 | (23.6) |
| Methylcyclopentane | 0 to 20 | (3.8) |
| Cyclohexane | 0 to 20 | (2.4) |
| Benzene | 0 to 10 | (1.3) |
| $C_7$ and higher | 0 to 10 | (2.5) |

As is well known from the above-mentioned U.S. Pat. Nos. 2,966,528 and 3,755,144, hydrogen and the hydrocarbon feed are contacted in the reaction zone with an isomerization catalyst. The catalyst composites that can be used in the isomerization zone include traditional isomerization catalyst. Such catalysts include high chloride catalyst on an alumina base containing platinum, and crystalline aluminosilicates or crystalline zeolites. Suitable catalyst compositions of this type will exhibit selective and substantial isomerization activity under the operating conditions of the process. Chlorided platinum alumina catalysts, such as disclosed in the above patents and U.S. Pat. Nos. 3,442,794 and 3,836,597 are preferred because of the significantly lower hydrogen to hydrocarbon ratio made possible in the isomerization zone. Additional benefits can be achieved with chloride platinum catalysts under conditions disclosed in U.S. Pat. No. 4,804,803, issued to Schmidt et al, whereby facilities for recovering and recycling hydrogen can be eliminated.

In the isomerization zone, the paraffins and monoalkyl paraffins, primarily monomethyl paraffins, in the feed stream are preferably converted to dialkyl, i.e., primarily dimethyl paraffins, which have the highest octane rating. Operating conditions within the isomerization zone, selected to maximize production of di-branched alkanes, include temperatures in the range of 40° to 235° C. and pressures in the range of 7 to 70 bars (g). Lower temperatures within the range are preferred since they favor equilibrium mixtures having higher concentrations of di-branched alkanes.

The isomerization zone may include a two-reactor system with a first stage reactor and a second stage reactor in the reaction zone. The catalyst used in the process is distributed equally between the two reactors. It is not necessary that the reaction be carried out in two reactors, but the use of two reactors and specialized valving is advantageous because it allows partial replacement of the catalyst system without taking the isomerization unit off stream. For the short periods of time during which replacement of catalyst may be necessary, the entire flow of reactants may be processed through only one reaction vessel while catalyst is replaced in the other. The use of two reaction zones also aids in maintaining lower catalyst temperatures, since any exothermic reaction, such as hydrogenation of unsaturates, can be performed in a first reaction vessel with the rest of the reaction carried out in a final reaction vessel at more favorable temperature conditions.

The effluent from the reactors, sometimes referred to herein as isomerate, is significantly lower in normal paraffin content, i.e., n-$C_5$ and n-$C_6$, and significantly higher in iso-paraffins, e.g., iso-pentane and methyl pentanes, and dimethyl paraffins, e.g., 2,2-dimethyl butane and 2,3-dimethyl butane. Thus, the feed, including recycled raffinate, may contain about 0–3% (wt.) of dimethyl paraffins, typically from about 1 to 3% (wt.), while the isomerate will contain 6–30% (wt.) dimethyl paraffins.

The effluent from the reactors enters a stabilizer that removes light gases and butane from the effluent. The bottoms from the stabilizer enters the adsorption zone where it is contacted with an adsorbent. This process is especially suited for adsorption systems that use multiple ports for supplying the process streams to the adsorbent and divide the adsorbent into a plurality of zones for adsorbing di-branched paraffins, recovering normal and iso-paraffins, purifying the adsorbent, and desorbing the normal and iso-paraffins. A well-known process of this type is the countercurrent moving bed for simulating moving bed countercurrent flow systems. Such systems have a much greater separation efficiency than fixed molecular sieve bed systems. In the moving bed or simulated moving bed processes, the retention and displacement operations are continuously taking place which allows both continuous production of an extract and a raffinate stream and the continuous use of feed and displacement fluid streams. One preferred embodiment of this process utilizes what is known in the art as the simulated moving bed countercurrent flow system. The operating principles and sequence of such flow system are described in U.S. Pat. No. 2,985,589 incorporated herein by reference. In such a system, it is the progressive movement of multiple liquid access points down a molecular sieve chamber that simulates the upward movement of molecular sieve contained in the chamber.

A number of specially defined terms are used in describing the simulated moving bed processes. The term "feed stream" indicates a stream in the process through which feed material passes to the molecular sieve. A feed material comprises one or more extract components and one or more raffinate components. An "extract component" is a compound or type of compound that is more selectively retained by the molecular sieve while a "raffinate component" is a compound or type of compound that is less selectively retained. In this process, di-branched hydrocarbons from the feed stream are extract components while feed stream normal and mono-branched hydrocarbons are raffinate components. The term "displacement fluid" or "desorbent" shall mean generally a material capable of displacing an extract component. The term "desorbent input stream" indicates the stream through which desorbent passes to the molecular sieve. The term "raffinate output stream" means a stream through which most of the raffinate components are removed from the molecular sieve. The composition of the raffinate stream can vary from about 100% desorbent to essentially 100% raffinate components. The term "extract stream" or "extract output stream" shall mean a stream through which an extract material which has been displaced by desorbent is removed from the molecular sieve. The composition of the extract stream can also vary from about 100% desorbent to essentially 100% extract components.

The term "selective pore volume" of the molecular sieve is defined as the volume of the molecular sieve which selectively retains extract components from the feedstock. The term "non-selective void volume" of the molecular sieve is the volume of the molecular sieve which does not selectively retain extract components from the feedstock. This volume includes the cavities of the molecular sieve which are capable of retaining raffinate components and the interstitial void spaces between molecular sieve particles. The selective pore volume and the non-selective void volume are generally expressed in volumetric quantities and are of importance in determining the proper flow rates of fluid required to be passed into an operational zone for efficient operations to take place for a given quantity of molecular sieve.

When molecular sieve "passes" into an operational zone (hereinafter defined and described) its non-selective void volume together with its selective pore volume carries fluid into that zone. The non-selective void volume is utilized in determining the amount of fluid which should pass into the same zone in a countercurrent direction to the molecular sieve to displace the fluid present in the non-selective void volume. If the fluid flow rate passing into a zone is smaller than the non-selective void volume rate of molecular sieve material passing into that zone, there is a net entrainment of liquid into the zone by the molecular sieve. Since this net entrainment is a fluid present in a non-selective void volume of the molecular sieve, it, in most instances, comprises less selectively retained feed components.

In the preferred simulated moving bed process only four of the access lines are active at any one time: the feed input stream, desorbent inlet stream, raffinate outlet stream, and extract outlet stream access lines. Coincident with this simulated upward movement of the solid molecular sieve is the movement of the liquid occupying the void volume of the packed bed of molecular sieve. So that countercurrent contact is maintained, a liquid flow down the molecular sieve chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the molecular sieve chamber into separate zones, each of which has a different function. In this embodiment of the process, it is generally necessary that three separate operational zones be present in order for the process to take place although in some instances an optional fourth zone may be used.

The adsorption zone, zone I, is defined as the molecular sieve located between the feed inlet stream and the raffinate outlet stream. In this zone, the feedstock contacts the molecular sieve, an extract component is retained, and a raffinate stream is withdrawn. Since the general flow through zone I is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in adsorption zone I is the purification zone II. The purification zone II is defined as the molecular sieve between the extract outlet stream and the feed inlet stream. The basic operations taking place in zone II are the displacement from the non-selective void volume of the molecular sieve of any raffinate material carried into zone II by the shifting of molecular sieve into this zone and the displacement of any raffinate material retained within the selective pore volume of the molecular sieve. Purification is achieved by passing a portion of extract stream material leaving zone III into zone II at zone II's upstream boundary to effect the displacement of raffinate material The flow of liquid in zone II is in a downstream direction from the extract outlet stream to the feed inlet stream.

Immediately upstream of zone II with respect to the fluid flowing in zone II is the desorption zone III. The desorption zone III is defined as the molecular sieve between the desorbent inlet and the extract outlet streams. The function of the desorption zone is to allow a desorbent which passes into this zone to displace the extract component which was retained in the molecular sieve during a previous contact with feed in zone I in a prior cycle of operation. The flow of fluid in zone III is essentially in the same direction as that of zones I and II.

In some instances, an optional buffer zone, zone IV, may be utilized. This zone, defined as the molecular sieve between the raffinate outlet stream and the desorbent inlet stream, if used, is located immediately upstream with respect to the fluid flow to zone III. Zone IV would be utilized to conserve the amount of desorbent utilized in the desorption step since a portion of the raffinate stream which is removed from zone I can be passed into zone IV to displace desorbent present in that zone out of the zone into the desorption zone. Zone IV will contain enough desorbent so that raffinate material present in the raffinate stream passing out of zone I and into zone IV can be prevented from passing into zone III thereby contaminating extract stream removed from zone III. In the instances in which the fourth operational zone is not utilized, the raffinate stream passed from zone I to zone IV must be carefully monitored in order that the flow directly from zone I to zone III can be stopped when there is an appreciable quantity of raffinate material present in the raffinate stream passing from zone I into zone III so that the extract outlet stream is not contaminated.

A cyclic advancement of the input and output streams through the fixed bed of molecular sieve can be accomplished by utilizing a manifold system in which the valves in the manifold are operated in a sequential manner to effect the shifting of the input and output streams thereby allowing a flow of fluid with respect to solid molecular sieve in a countercurrent manner. Another mode of operation which can effect the countercurrent flow of solid molecular sieve with respect to fluid involves the use of a rotating disc valve in which the input and output streams are connected to the valve and the lines through which feed input, extract output, desorbent input and raffinate output streams pass are advanced in the same direction through the molecular sieve bed. Both the manifold arrangement and disc valve are known in the art. Specifically, rotary disc valves which can be utilized in this operation can be found in U.S. Pat. Nos. 3,040,777 and 3,422,848, incorporated herein by reference. Both of the aforementioned patents disclose a rotary type connection valve in which the suitable advancement of the various input and output streams from fixed sources can be achieved without difficulty.

In many instances, one operational zone will contain a much larger quantity of molecular sieve than some other operational zone. For instance, in some operations, the buffer zone can contain a minor amount of molecular sieve as compared to the molecular sieve required for the adsorption and purification zones. It can also be seen that in instances in which desorbent is used which can easily displace extract material from the molecular sieve that a relatively small amount of molecular sieve will be needed in the desorption zone as compared to the molecular sieve needed in the adsorption zone or purification zone. Since it is not required that the molecular sieve be located in a single column, the use of multiple chambers or a series of columns is within the scope of the invention.

It is not necessary that all of the input or output streams be simultaneously used, and, in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

In the typical operation of this process, at least a portion of the raffinate output stream and a portion of the extract output stream will be passed to a separation means wherein at least a portion of the desorbent can be separated to produce a desorbent stream which can be reused in the process and raffinate and extract products containing a reduced concentration of desorbent. The separation means will typically be a fractionation column, the design and operation of which is well known to the separation art.

Reference can be made to D. B. Broughton U.S. Pat. No. 2,985,589, and to a paper entitled "Continuous Adsorptive Processing-A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Although both liquid and vapor phase operations can be used in many adsorptive type separation processes, liquid-phase operation is preferred for this process because of the lower temperature requirements and because of the higher yields of extract product that can be obtained with liquid-phase operation over those obtained with vapor-phase operation. Adsorption conditions will, therefore, include a pressure sufficient to maintain liquid phase. Adsorption conditions will include a temperature range of from about 60° C. to about 200° C., with about 100° C. to about 180° C. being preferred and a pressure sufficient to maintain liquid-phase, ranging from about atmospheric to about 500 psig with from about atmospheric to about 200 psig usually being adequate. Desorption conditions will include the same range of temperatures and pressures as used for adsorption conditions.

The feed to the separation zone is the effluent of the isomerization zone from which hydrogen gas may be removed and recycled to the isomerization reaction and light materials. Feed components and concentration may be in the ranges set forth in the following Table 2 along with a typical feed composition.

TABLE 2

| Component | Research Octane No. (RON) | Typical Composition (wt. %) | Range (wt. %) |
|---|---|---|---|
| propane |  | 0.1 | 0–0.2 |
| i-butane | 100+ | 0.9 | 0–5 |
| n-butane | 93.6 | 0.1 | 0–5 |
| i-pentane | 92.3 | 28.1 | 20–50 |
| n-pentane | 61.7 | 8.6 | 5–20 |
| cyclopentane | 100.0 | 1.6 | 0–3 |
| 2,2-dimethyl butane | 91.8 | 14.9 | 5–25 |
| 2,3-dimethyl butane | 101.7 | 4.8 | 2–10 |
| 2-methyl pentane | 73.4 | 13.7 | 10–20 |
| 3-methyl pentane | 74.5 | 7.8 | 5–15 |
| n-hexane | 24.8 | 5.2 | 2–10 |
| methyl cyclopentane | 91.3 | 5.4 | 0–10 |
| cyclohexane | 83.0 | 7.2 | 0–10 |
| C$_7$+ | 100+ | 1.7 | 0–5 |
|  |  | 100.1 |  |

The adsorbent used in the invention has the capability of selectively adsorbing the di-branched paraffins and rejecting the normal and mono-branched paraffins. Prior processes, such as taught in the above-mentioned patents, U.S. Pat. Nos. 4,717,784 and 4,855,529, have rejected di-branched paraffins and adsorbed normal and mono-branched paraffins. The large pore adsorbents of the invention, capable of selectively adsorbing the di-branched paraffins, are highly advantageous since they exhibit higher mass transfer rates of the adsorbed species and also have greater capacity than prior adsorbents. This former results in faster cycle times and more efficient separation. The latter increases the amount of adsorbate that can be adsorbed in each cycle. In addition, the lower octane components, being in greater volume in the isomerate results in a more efficient process since the non-adsorbed components pass directly through the adsorbent while the components in lower volume are adsorbed and desorbed during each cycle, thereby decreasing the adsorbent required for a given volume throughput of feed to the separation unit. The adsorbents capable of selectively adsorbing the di-branched paraffins and rejecting both monomethyl paraffins and normal paraffins are aluminophosphates from the group comprising SAPO-5, AlPO$_4$-5, and MAPSO-5, and MgAPO-5 and SSZ-24 (an all-silica molecular sieve that is isostructural with AlPO$_4$-5). All have low isosteric heats of adsorption for paraffins, e.g., for ethane in the range 5 to 6.2 KCal/mole determined at approximate fractional surface coverage (e), compared to 7.3 for NaX, 7.8 for AlPO$_4$-11, etc. SAPO-5 is a silicoaluminophosphate whose method of manufacture, structure and properties are disclosed in U.S. Pat. No. 4,440,871 to Lok et al. AlPO$_4$-5 is an aluminophosphate having a pore size of 8 Å and may be made by the method disclosed in U.S. Pat. No. 4,310,440 to Wilson et al. MgAPO-5 is a metalloaluminophosphate having the structural formula, properties and method of manufacture disclosed in U.S. Pat. No. 4,567,029 to Wilson et al. As described in U.S. Pat. No. 4,310,440, MAPSO-5 is a metallosilica aluminophosphate in which the metal is magnesium and whose structural formula, properties and method of manufacture are disclosed in U.S. Pat. No. 4,758,419 to Lok et al. SSZ-24 is isostructural with AlPO$_4$-5 and is described in Nordstrand et al supra and U.S. Pat. No. 4,834,958.

Typically, adsorbents used in separation processes, such as described herein, contain the crystalline material dispersed in an amorphous inorganic matrix or binder, having channels and cavities therein which enable liquid access to the crystalline material. Amorphous material such as silica, or silica-alumina mixtures or compounds, such as clays, are typical of such inorganic matrix materials. The preferred binder for the separation of this invention is bentonite clay. The binder, typically in amounts ranging from 2-25% by weight, aids in forming or agglomerating the crystalline particles of the zeolite which otherwise would comprise a fine powder. The adsorbent may thus be in the form of particles such as extrudates, aggregates, tablets, macrospheres or granules having a desired particle size range, from about 16 to 40 mesh (Standard U.S. Mesh) (1.9 mm to 230 μm).

In the separation of the present invention, it is preferred that the level of water content of the adsorbent be maintained below about 2% (LOI), and preferably below about 1% (LOI). In contrast to the faujasites, such as BaX (Neuzil U.S. Pat. No. 3,706,813), which selectively adsorb normal paraffins at low water content, exhibit a reversal of selectivity at about 6-8% (LOI) and at the higher levels of water selectively adsorb di-branched paraffins, the adsorbents of the invention lose capacity at higher water content.

In this process, and, particularly, the preferred continuous, simulated moving bed process, the desorbent must be selected to satisfy the following criteria: First, the desorbent material should displace an extract component from the adsorbent with reasonable mass flow rates without itself being so strongly adsorbed in the following adsorption cycle. Secondly, the desorbent material must be compatible with the particular adsorbent and the particular feed mixture. More specifically, it must not reduce or destroy the critical selectivity of the adsorbent for an extract component with respect to a raffinate component. The desorbent should additionally be easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be vary high nor would the desorbent material be available for reuse in the process. It is, therefore, contemplated that any desorbent material used in this process will preferably have a substantially different average boiling point than that of the feed mixture, i.e., more than about 5° C. difference, to allow separation of at least a portion of desorbent material from feed components in the extract and raffinate streams by simple fractional distillation, thereby permitting reuse of desorbent material in the process. Finally, desorbent materials should also be materials which are readily available and reasonable in cost. In the preferred isothermal, isobaric, liquid-phase operation of the process of our invention, we prefer $C_6$ to $C_{10}$ n-paraffins, e.g., n-hexane, n-heptane and n-decane, and especially prefer n-heptane as the desorbent material.

Neuzil et al U.S. Pat. No. 3,706,813, above, disclosed faujasites having water levels of 5-8% (LOI) as adsorbents for the separation of multi-branched paraffins from singly-branched and normal paraffins using desorbent materials similar to the feedstock components, e.g., multi-branched paraffins, singularly branched paraffins and normal paraffins and cycloparaffins. While multi- and singly-branched paraffins, such as iso-octane and 3-methyl pentane are excellent desorbents for the separation of n-paraffins from branched paraffins with a faujasite, such as Na-X, Ca-X or Ba-X, branched chain paraffins are so strongly adsorbed onto the present adsorbents that they show very little separation and make ineffective desorbents for the process of the invention. The desorbent strength of normal paraffins is even greater than the branched paraffins with faujasites, CaX and BaX. For example, the desorbent strength of several materials increases in the following order with dry CaX:

iso-octane (multi-branched) < 3-methyl pentane < n-decane < cyclooctane;

and in the following order with BaX:

iso-octane < n-octane < 2,3-DMP < MeCH < cyclooctane.

In the ranking above, 2,3-dimethyl pentane and methyl cyclohexane are abbreviated 2,3-DMP and MeCH, respectively. However, with the faujasites, no such criticality as was shown with the present adsorbents exists, since even cyclooctane, the strongest desorbent tested, nevertheless exhibits good selectivity between normal and branched paraffins on both CaX and BaX. It was also unexpected that isooctane, which is a well balanced desorbent on faujasites, is too strong for the adsorbents of the invention and that only normal paraffins from $C_6$ to $C_{10}$ were adequately balanced as desorbents to maintain the selectivity between di-branched paraffins and mono-branched and normal paraffins on the present adsorbents. The behavior of the aluminophosphate adsorbents in relation to the desorbents is unusual and illustrates the unpredictability of the desorbent on the adsorbent of choice for a particular separation. Thus, a feature of the invention is the discovery of a class of desorbents that are effective desorbents in this separation with aluminophosphate adsorbents.

A dynamic testing apparatus is employed to test various adsorbents with a particular feed mixture and desorbent material to measure the adsorption characteristics of retention, capacity and exchange rate. The apparatus used herein consisted of a helical adsorbent chamber of approximately either 70 cc or 14 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect qualitatively, or determine quantitatively, one or more components in the effluent stream leaving the adsorbent chamber. A pulse test, performed using this apparatus and the following general procedure, is used to determine data, e.g., selectivity, for various adsorbent systems. The adsorbent is placed in a chamber and filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent material is injected for a duration of several minutes. Desorbent material flow is resumed, and the tracer and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, adsorbent performance can be rated in terms of void volume, net retention volume (NRV) for an extract or a raffinate component, the rate of desorption of an extract component from the adsorbent and selectivity. The net retention volume of an extract or a raffinate component may be characterized by the distance between the center of the peak envelope of the extract or raffinate component and the center of the peak envelope of the tracer component (void volume) or some other known reference point. Gross retention volume (GRV) is the distance between the center of a peak envelope and the zero abscissa and measured as total ml. of desorbent material pumped during this interval. NRV is also the difference between the respective GRVs and the GRV of the tracer. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. Selectivity, $\beta$, is calculated as the ratio of the net retention volume of one of the components (reference) to that of each of the other components.

The examples shown below are intended to further illustrate the process of this invention without unduly limiting the scope and spirit of said process. The examples present test results for various adsorbent and desorbent materials when using the above dynamic testing apparatus.

EXAMPLE I

In this experiment, three pulse tests, as described above, were performed to evaluate the present invention in separating high octane components from an isomerization reaction product stream with SAPO-5 adsorbent. The desorbent was n-heptane.

In the first pulse test, the column was filled with 70 cc of the adsorbent mentioned above bonded with bentolite clay and calcined at 600° C. for 3 hours to a water content of 0.7% (LOI). The temperature in the column was maintained at 120° C. and the pressure was sufficient to provide liquid-phase operations. The feed mixture employed for this test was the isomerate having the composition (typical) of Table 2. The desorbent material was run continuously at a nominal liquid hourly space velocity (LHSV) of 1.2 $hr^{-1}$ which amounted to a flow rate of about 1.42 cc of desorbent per minute. At some convenient time interval, the desorbent was stopped and 5.0 cc of the feed mixture was run for a 3.5 minute interval at a rate of 1.42 cc per minute. The desorbent stream was then resumed at the same LHSV and continued to pass into the adsorbent column until all of the feed components had been eluted from the column as determined by observing the chromatograph generated by the effluent material leaving the adsorption column. The sequence of operations usually takes about an hour. The pulse of feed and subsequent desorption may be repeated in sequence as often as is desired. The chromatographic data obtained from the pulse test is set forth in Table 3, under the headings gross retention volume (GRV), net retention volume (NRV) and selectivity ($\beta$).

TABLE 3

| Component | Extract (wt. %) | GRV | NRV | $\beta$ (2,3-DMB) |
|---|---|---|---|---|
| Butane | 0.1 | 45.1 | 0.0 | ∞ |
| Hexane | 6.01 | 47.6 | 2.5 | 4.88 |
| Pentane | 9.45 | 48.5 | 3.4 | 3.59 |
| 2-Methyl Pentane | 14.91 | 49.0 | 3.9 | 3.13 |
| 3-Methyl Pentane | 8.66 | 50.6 | 5.5 | 2.18 |
| Isobutane | 0.93 | 50.9 | 5.8 | 2.10 |
| Iso-pentane | 19.67 | 51.7 | 6.6 | 1.85 |
| Methyl Cyclopentane | 5.82 | 55.3 | 10.2 | 1.20 |
| 2,2-DMB | 15.81 | 56.3 | 11.2 | 1.09 |
| 2,3-DMB | 6.85 | 57.3 | 12.2 | 1.00 (Reference) |
| Cyclohexane | 8.17 | 58.5 | 13.4 | 0.91 |

EXAMPLE II

Additional pulse tests were performed with other adsorbents and desorbents of the invention under the same conditions as Example 1, except that 14.4 cc adsorbent was used in a smaller column, the desorbent flow rate was 0.85 cc/min in the first pulse test and 0.98 cc/min. in the second and the temperature was 120° C. Each feed pulse was 1.0 cc of equal parts of components in the mixture set forth in Tables 4 and 5, respectively, diluted with 90 wt. % of the desorbent. In the first pulse test, the adsorbent used was AlPO$_4$-5 dried (calcined) to a water content of 0.9% (LOI at 900° C.). In the second pulse test, the adsorbent used was MgAPSO-5 at an LOI of 0.93% at 900° C. In third and fourth pulse tests, which were run identically to the second, except that the LOI was 3.83% and 4.47%, respectively, the same selectivity was observed, but the adsorbent capacities were greatly reduced. In the results shown for the first and second pulse tests in Tables 4 and 5, respectively, the selectivity of AlPO$_4$-5 and MAPSO-5 for di-branched paraffins and non-adsorption of normal paraffins and mono-branched paraffins is also observed. Thus, the high octane components, 2,2-DMB and 2,3-DMB were adsorbed by the adsorbent and desorbed by a desorbent, n-heptane, and can be recovered in the extract stream of an adsorption separation column while the non-adsorbed low octane components, primarily 2-methyl pentane and normal paraffins are less strongly adsorbed (relatively non-adsorbed) and can be recovered in the raffinate stream of the adsorption separation column.

TABLE 4

AlPO$_4$-5 ADSORBENT

| Component | GRV | NRV | β (2,3 DMB) |
|---|---|---|---|
| N-Nonane | 16.0 | 0.0 | ∞ |
| Mesitylene | 16.1 | 0.1 | 35 |
| n-Hexane | 16.1 | 0.1 | 35 |
| 2 Methyl Pentane | 16.3 | 0.3 | 7.7 |
| 2,2-DMB | 17.6 | 1.5 | 1.45 |
| 2,3-DMB | 18.3 | 2.2 | 1.00 (Reference) |
| Iso-octane | 18.3 | 2.2 | 0.99 |

TABLE 5

MAPSO-5 ADSORBENT

| Component | GRV | NRV | β (2,3 DMP) |
|---|---|---|---|
| n-Hexane | 14.9 | 0.0 | ∞ |
| n-Pentane | 15.0 | 0.1 | 36 |
| 2-Methyl Pentane | 15.2 | 0.3 | 12 |
| Iso-pentane | 16.0 | 1.1 | 3.27 |
| 2,2-DMB | 17.5 | 2.7 | 1.33 |
| Iso-octane | 17.8 | 2.9 | 1.24 |
| 2,3-DMB | 18.5 | 3.6 | 1.00 (Reference) |

A fifth pulse test was run under the same conditions as the first three, except that the adsorbent was SAPO-5 and the desorbent was decane (n-C$_{10}$). The column flow rate was 0.75 cc/min. The results were similar and are set forth in the following Table 6.

TABLE 6

| Component | GRV | NRV | β (2,3 DMP) |
|---|---|---|---|
| n-Hexane | 11.7 | 0.0 | ∞ |
| N-Pentane | 11.8 | 0.1 | 16 |
| Iso-pentane | 12.3 | 0.6 | 2.67 |
| 2,2-DMB | 12.7 | 1.0 | 1.60 |
| Iso-octane | 12.8 | 1.1 | 1.45 |
| Cyclohexane | 13.2 | 1.5 | 1.07 |
| 2,3-DMB | 13.3 | 1.6 | 1.00 (Reference) |

What is claimed is:

1. A process for producing a high octane hydrocarbon stream comprising:
   (a) introducing a paraffin hydrocarbon feed stream comprising C$_{4-6}$ paraffins into an isomerization zone maintained at isomerization conditions and containing an isomerization catalyst;
   (b) contacting said feed stream with said catalyst to produce an isomerate comprising dimethyl paraffins, monomethyl paraffins and normal paraffins;
   (c) passing said isomerate to a separation zone and contacting said isomerate with an adsorbent having pores large enough to admit all components of said isomerate and having selectivity for preferentially adsorbing said dimethyl paraffins and not adsorbing said monomethyl paraffins and normal paraffins, said adsorbent being selected from the group consisting of AlPO$_4$-5, SAPO-5, SSZ-24, MgAPO-5 and MAPSO-5 and containing less than about 2% water, measured by loss on ignition (LOI) at 900° C.;
   (d) removing a first stream comprising said non-adsorbed monomethyl paraffins and normal paraffins;
   (e) introducing a desorbent comprising a paraffin hydrocarbon having from 6–10 carbon atoms in the molecule to said separation zone to desorb said adsorbed dimethyl paraffins from said adsorbent;
   (f) recovering a second stream comprising said desorbed dimethyl paraffins; and
   (g) recycling said first stream to said isomerization zone.

2. The process of claim 1 wherein said water content is below 1%.

3. The process of claim 1 where said first stream additionally contains isopentane and said desorbent and said first stream is introduced into a fractionation zone wherein said iso-pentanes and desorbent are removed from said first stream and collected separately and the remaining monomethyl paraffins and normal paraffins in said first stream are recycled to said isomerization zone.

4. A continuous process for separating dimethyl paraffins (DMP's) from a feed mixture containing DMP's, monomethyl paraffins and normal paraffins comprising contacting at adsorption conditions, said feed mixture with an adsorbent selected from the group consisting of AlPO$_4$-5, SAPO-5, SSZ-24, MgAPO-5 and MAPSO-5 and containing less than 2% water, measured by loss on ignition (LOI) at 900° C., to selectively adsorb said DMP's, removing said non-adsorbed monomethyl paraffins and normal paraffins from said adsorbent, desorbing said adsorbed DMP's from said adsorbent with a desorbent comprising a paraffin hydrocarbon having from 6–10 carbon atoms in the molecule.

5. The process of claim 4 wherein said desorbent is n-heptane.

* * * * *